United States Patent [19]

Takeuchi

[11] Patent Number: 4,881,212

[45] Date of Patent: Nov. 14, 1989

[54] ULTRASONIC TRANSDUCER

[75] Inventor: Yasuhito Takeuchi, Tokyo, Japan

[73] Assignee: Yokogawa Medical Systems, Limited, Tokyo, Japan

[21] Appl. No.: 270,157

[22] PCT Filed: Apr. 24, 1987

[86] PCT No.: PCT/JP87/00265

§ 371 Date: Oct. 18, 1988

§ 102(e) Date: Oct. 18, 1988

[87] PCT Pub. No.: WO87/06790

PCT Pub. Date: Nov. 5, 1987

[30] Foreign Application Priority Data

Apr. 25, 1986 [JP] Japan .................................. 61-96549

[51] Int. Cl.$^4$ ............................................. H04R 1/02
[52] U.S. Cl. ................................. 367/152; 310/336
[58] Field of Search ................... 310/334, 336; 73/644; 367/140, 157, 152

[56] References Cited

U.S. PATENT DOCUMENTS

| | | | |
|---|---|---|---|
| 3,979,565 | 9/1976 | McShane | 310/336 X |
| 4,366,406 | 12/1982 | Smith et al. | 310/336 X |
| 4,523,122 | 6/1985 | Tone et al. | 310/334 |
| 4,594,897 | 6/1986 | Bantz | 310/336 |
| 4,659,956 | 4/1987 | Trzaskos et al. | 310/335 |
| 4,749,900 | 6/1988 | Hadimioglu et al. | 310/334 |
| 4,795,935 | 1/1989 | Fujii et al. | 310/336 |

FOREIGN PATENT DOCUMENTS

| | | | |
|---|---|---|---|
| 2746712 | 4/1978 | Fed. Rep. of Germany | 310/334 |
| 119998 | 7/1984 | Japan | 310/336 |

Primary Examiner—Brian S. Steinberger
Attorney, Agent, or Firm—Moonray Kojima

[57] ABSTRACT

This invention is basically, an ultrasonic transducer that can be configured with good reproducibility, that includes an acoustic impedance matching member that gradually changes the acoustic impedance, and which is characterized by An acoustic impedance matching member(2) configured with multiple unit layers (21, 22, 23, ... 2n), each layer being thinner than a quarter-wavelength of an ultrasonic wave, and each unit layer having a laiminated structure make up of heavy metal(52) and plastic(51) layers with a thickness ratio set between them to change gradually from the unit layer close to the ultrasonic oscillator to the unit layer close to the subject.

5 Claims, 2 Drawing Sheets

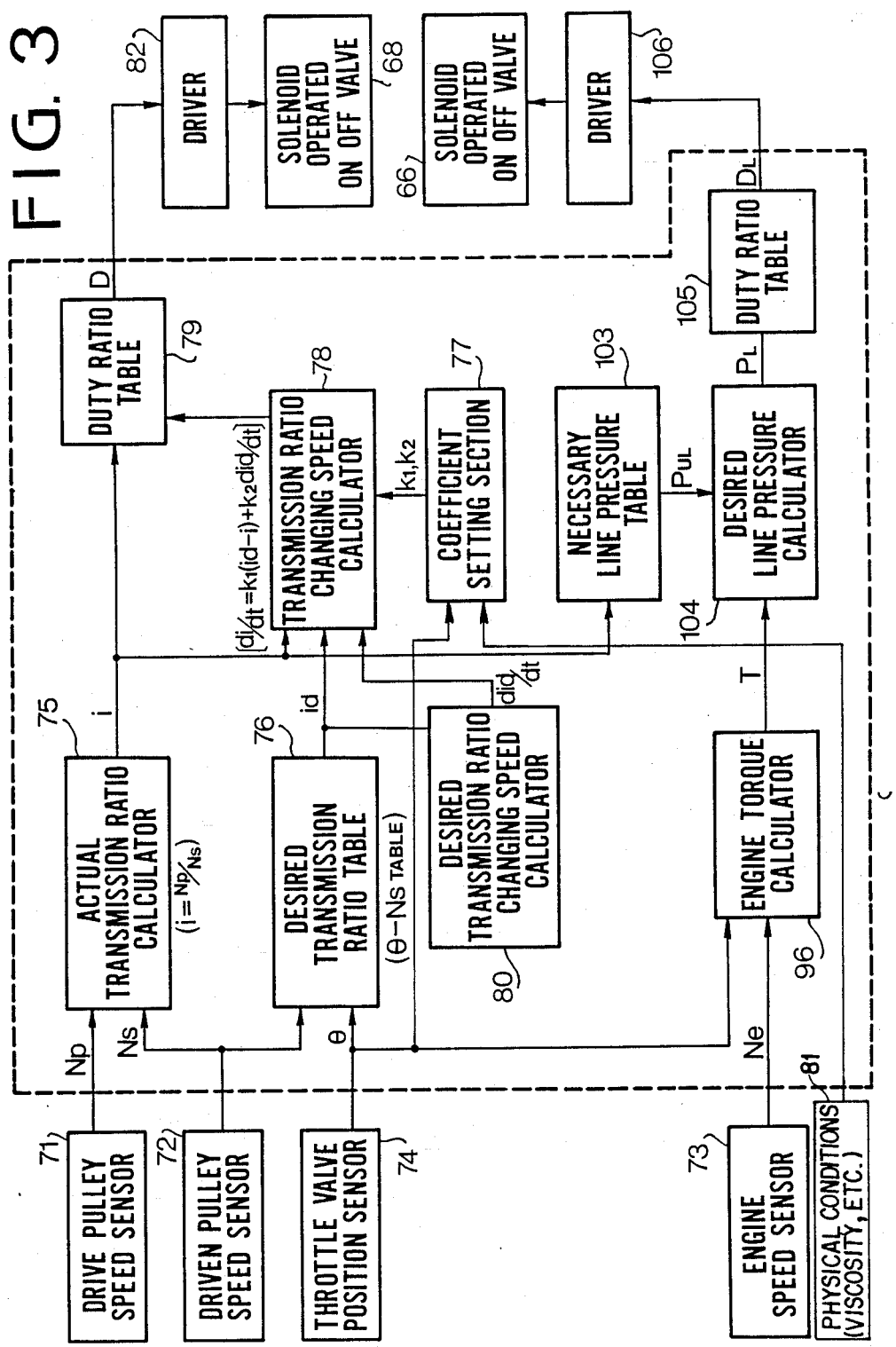

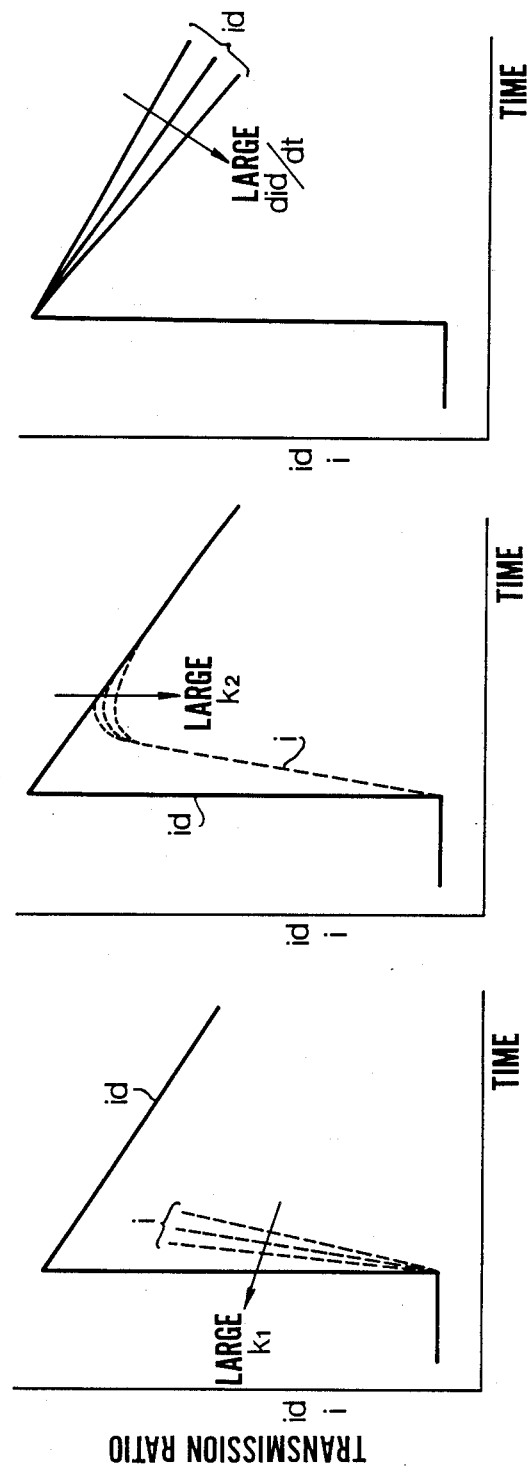

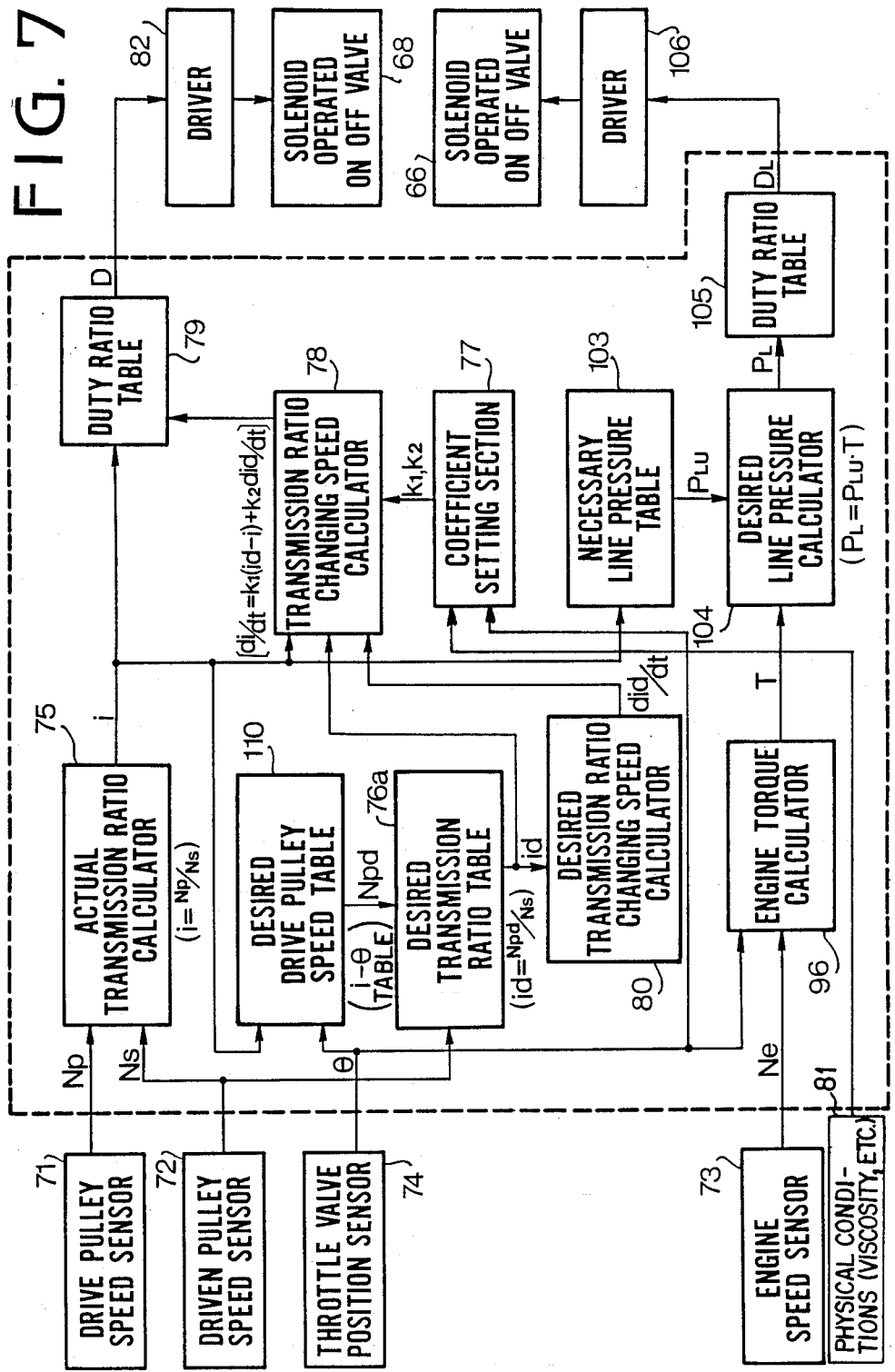

ULTRASONIC TRANSDUCER

(TECHNICAL FIELD)

This invention is basically an improved broadband ultrasonic transducer designed for medical or industrial applications. More specifically, it is an ultrasonic transducer with better acoustic impedance matching between an ultrasonic oscillator and the surface of a subject.

(BACKGROUND ART)

FIG. 6 is a sectional view of a conventional ultrasonic transducer configuration (prior art). In the figure, number 1 indicates an ultrasonic oscillator, 2 indicates an acoustic impedance matching member installed in front, 3 indicates an acoustic damper, and 4 indicates the subject.

Conventionally, a member having a thickness equivalent to a single or three-layer quarter-wavelength plate is used for acoustic impedance matching layer 2. The energy transmission efficiency and bandwidth are both improved when the number of quarter wavelength plates and the acoustic impedance of the material are properly selected. It is also known, however, that an acoustic impedance matching layer consisting of n layer of a quarter-wavelength plate fails to obtain a major additive effect as compared to when n=2 if n is made n > or = 3.

Therefore, an improved version of acoustic impedance matching layer 2 is proposed (as noted in published Patent No. Showa 58-18095) that successively changes the acoustic impedance between the respective layers in contact with ultrasonic oscillator 1 and the surface of the subject. However, it is not easy to actually produce a composite material having a gradually changing acoustic impedance, or if produced, a lack of reproducibility poses a problem.

(DISCLOSURE OF THE INVENTION)

The object of this invention is to provide a ultrasonic transducer that better matches the ultrasonic oscillator with a subject by providing an acoustic matching layer of good reproducibility that gradually changes acoustic impedance.

(METHOD OF SOLVING THE PROBLEM)

To use our invention in the preferred application mode, we employed an ultrasonic transducer, consisting of an ultrasonic oscillator and an impedance matching member installed on the ultrasonic radiation surface, characterized by the impedance matching member having a multilayer configuration of unit layers, each thinner than a quarter-wavelength. Each unit layer also has a laminated structure consisting of heavy metal and plastic layers with their layer thickness factor being set to increase gradually in order from the unit layer in contact with the ultrasonic oscillator to the other unit layer in contact with the subject.

(BRIEF DESCRIPTIONS OF DRAWINGS)

(BEST MODE FOR CARRYING OUT THE INVENTION)

Figure 1:
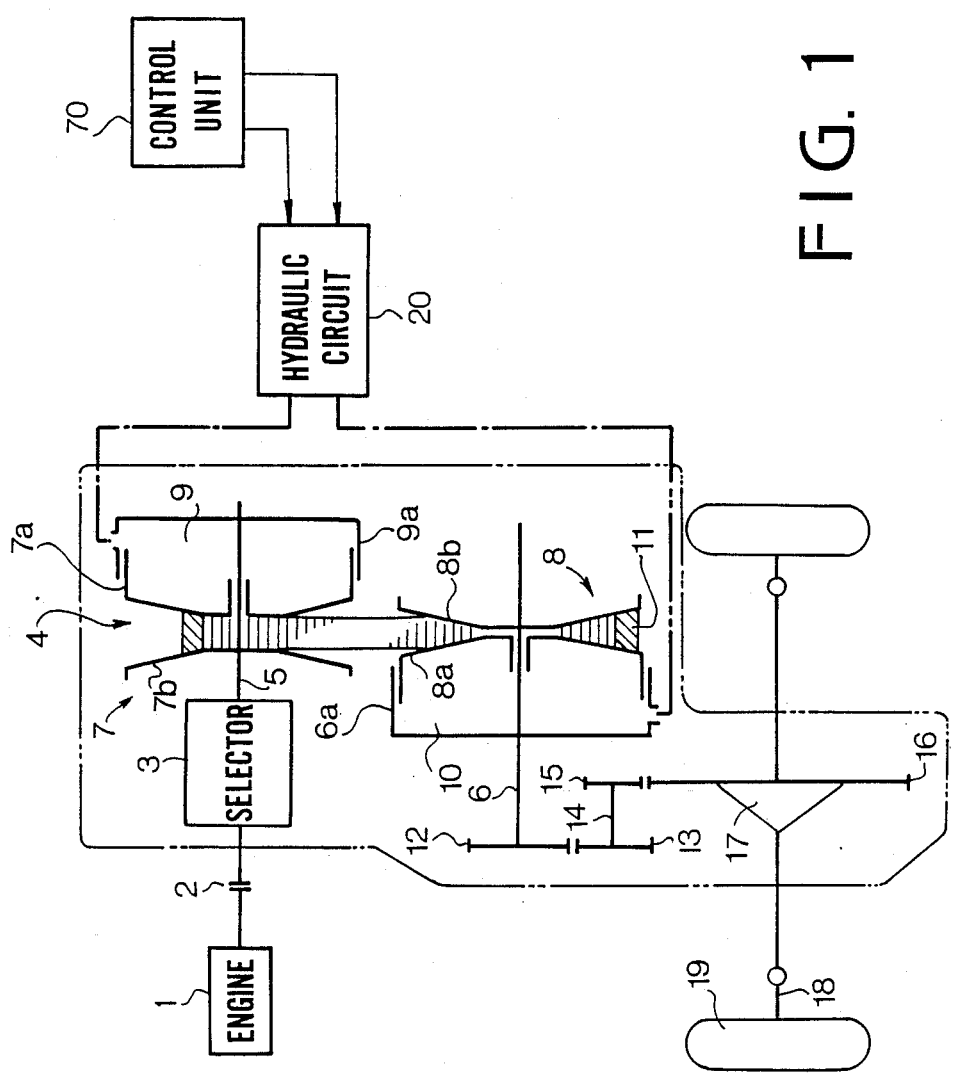
FIG. 1 is the schematic sectional view of the preferred application mode of the ultrasonic transducer based on this invention.
Figure 2A:
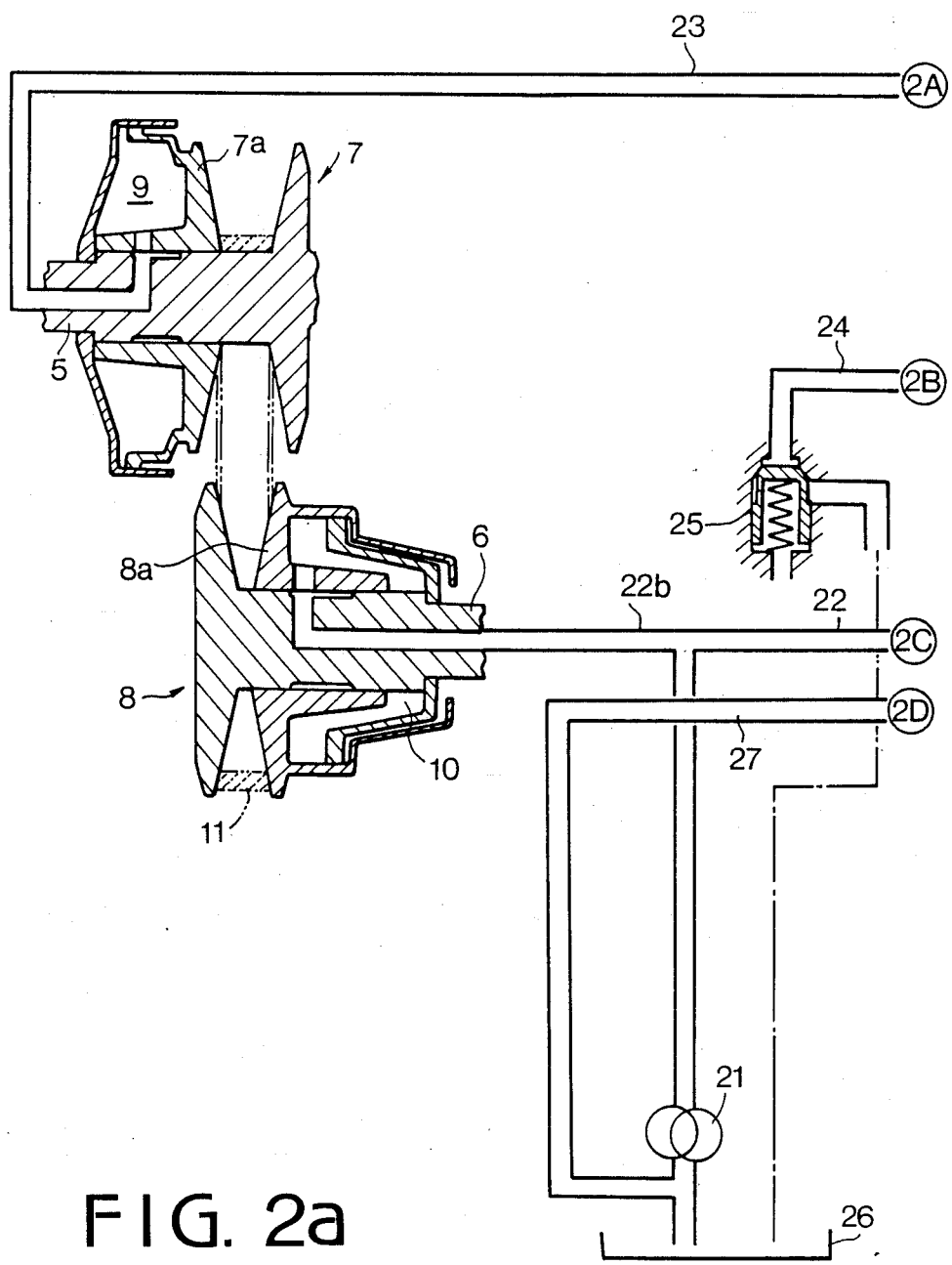
FIGS. 2 and 3 are sectional views of individual unit layers that make up the acoustic impedance matching member shown in FIG. 1.
Figure 2B:
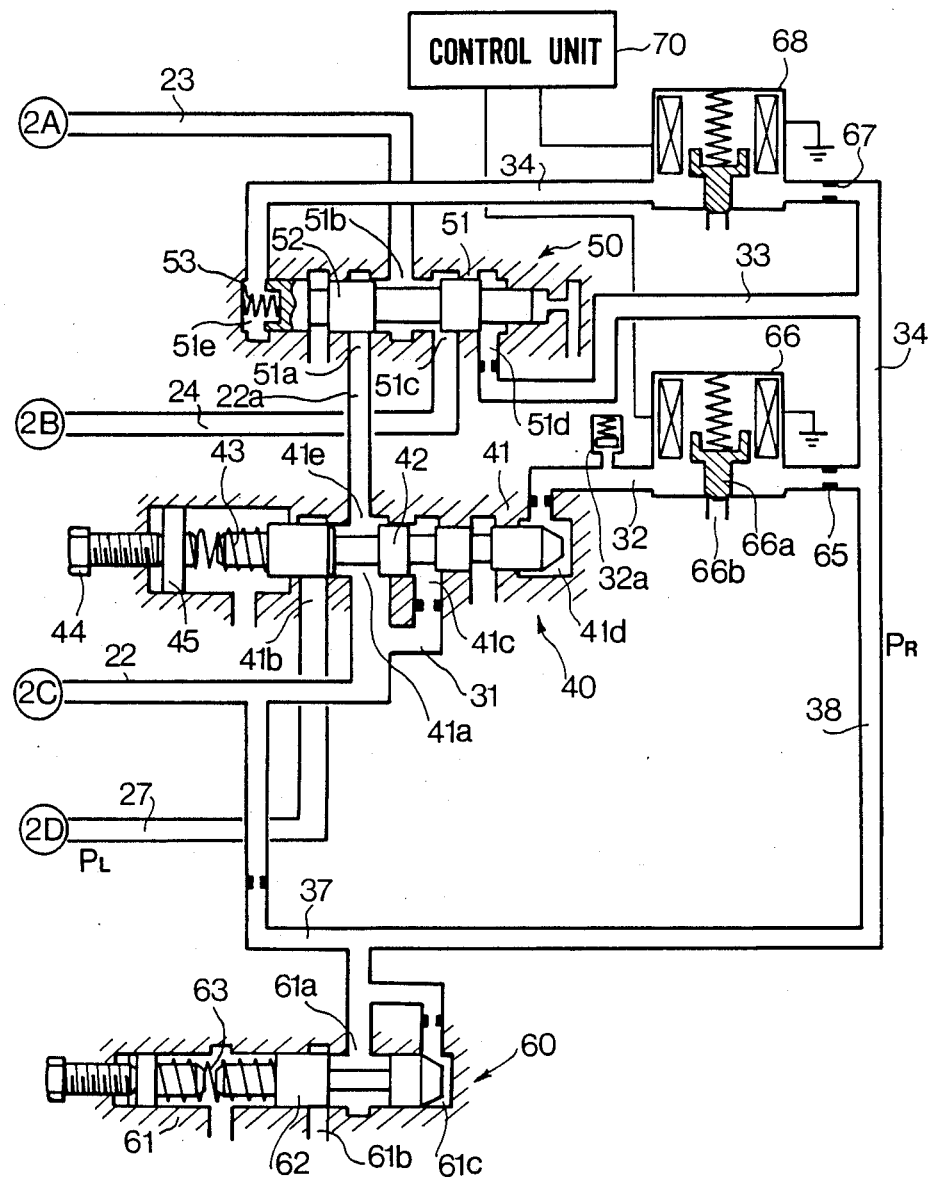

An example of the preferred application mode of this invention is described as follows in detail by referring to the drawings.

Figure 2:
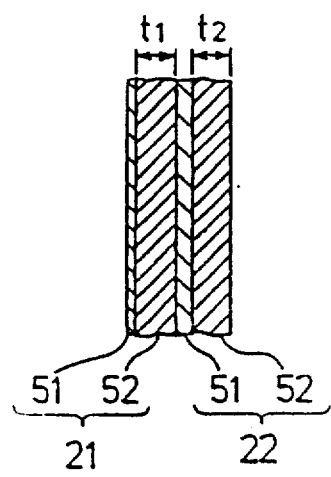
Figure 3:
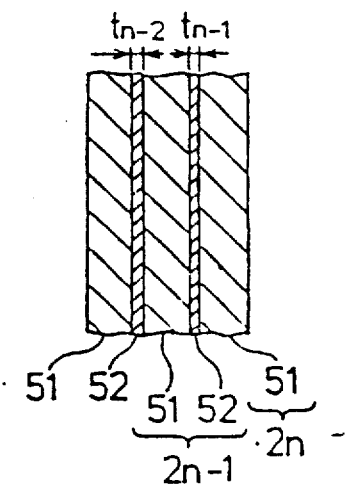
Figure 4:
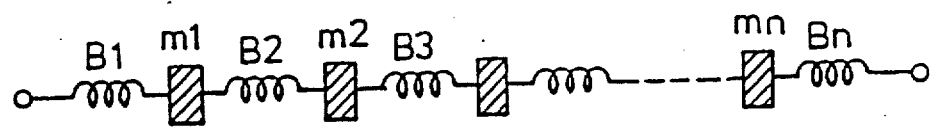
Figure 5:
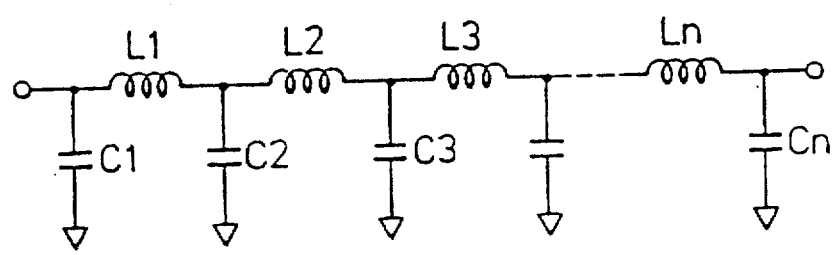
Figure 6:
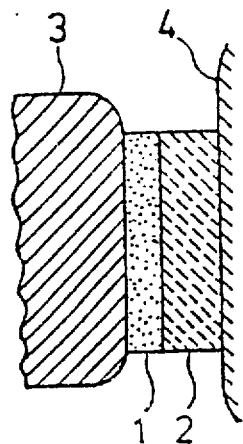
FIG. 6 shows the schematic sectional view of a conventional ultrasonic transducer (prior art).

In FIG. 1, number 1 indicates an ultrasonic oscillator consisting of PZT and other components, 2 indicates an acoustic impedance matching member (that characterizes this invention) installed in front of ultrasonic oscillator 1 (ultrasonic wave radiation surface), 3 indicates an acoustic damper installed on back of ultrasonic oscillator 1, and 4 indicates the subject. Acoustic impedance matching member 2 consists of the 21, 22, ... 2n laminated unit layers, each of which is thinner than a quarter-wavelength (for example, approx. lambda/10 to 20) and laminated to each other using a normal application of adhesion or heat adhesion. FIGS. 2 and 3 are sectional views showing more detailed configuration of each unit layer that makes up the acoustic impedance matching member. FIG. 2 shows the layers close to the end in contact with ultrasonic oscillator 1, and FIG. 3 shows the layers close to the end in contact with subject 4. In these figures, 51 indicates a plastic layer consisting of mylar, polyester, polyolefine, and other elements. The number 52 indicates a heavy metal layer (deposited on top of plastic film layer 51) that consists of, for example, copper, chromium, nickel, iron, cobalt, and other metals and their oxides, nitrides, and other heavy substances (atoms or particles). The thickness factor of heavy metal layer 52 against plastic layer 51 is set to change in order from the unit layer close to the end in contact with ultrasonic oscillator 1 to the unit layer close to the other end in contact with subject 4. In other words, thickness $t_1, t_2, \ldots t_n$ of heavy metal layer 52 (in the unit layer) is structured to decrease as it moves away from ultrasonic oscillator 1 ($t_1 > t_2 > t_3 > \ldots > t_{n-1} > t_n = 0$) when the subject is a human body. Conversely, the thickness of plastic film layer 51 is configured in the opposite way. Layer $2n$ in contact with subject 4 is only configured with plastic film layer 51.

Now, the function of acoustic impedance matching member 2 (with the above-described configuration) is explained as follows by referring to FIGS. 4 and 5.

Figure 4:
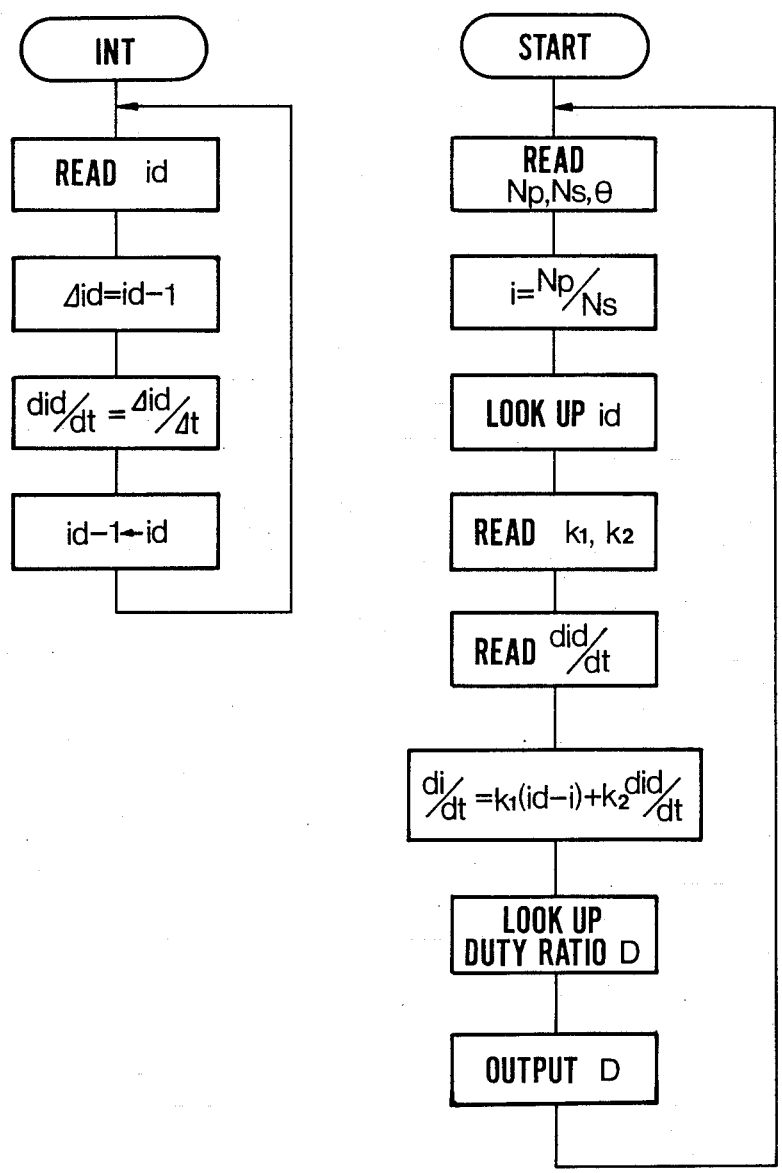
FIGS. 4 and 5 show the acoustic equivalent circuit of the acoustic impedance matching member shown in FIG. 1.
Figure 5:
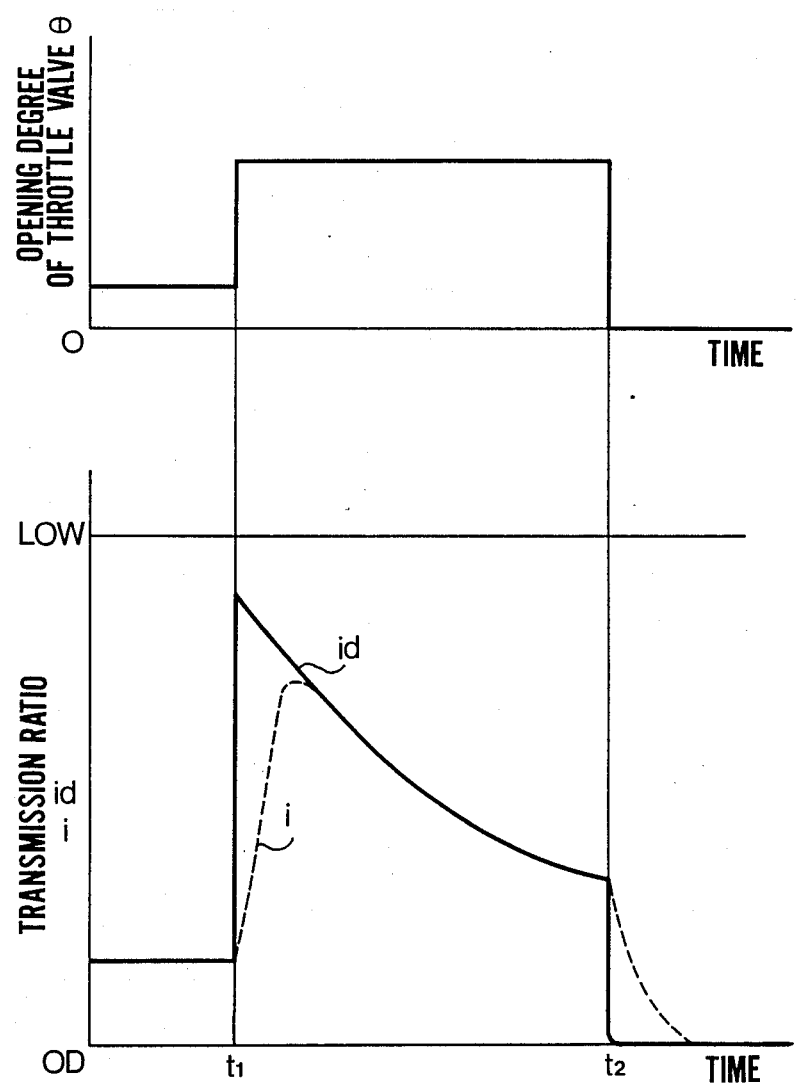
Figure 8:
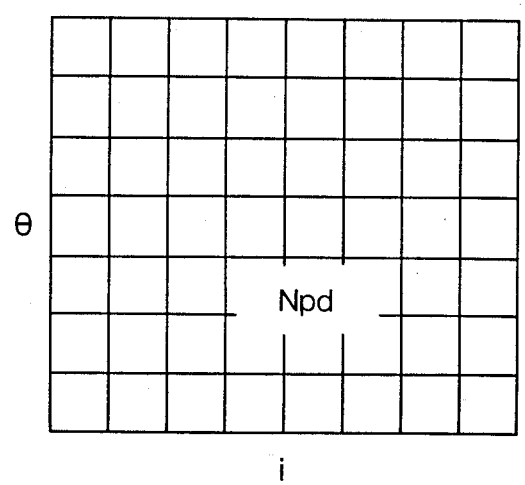
Figure 1:
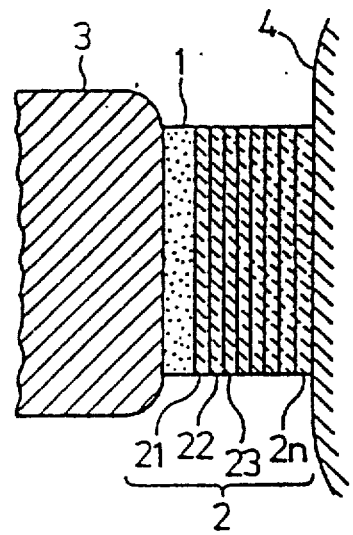

FIGS. 4 and 5 show the mechanical and electrical representations of the acoustic equivalent circuit of acoustic impedance matching member 2. Mechanically, the equivalent circuit is expressed by masses m1, m2, m3, ... and the springs (compliances) B1, B2, B3, ... in series connection. Electrically, it shows a filter circuit consisting of inductance L1, L2, L3, ... and capacitors C1, C2, C3, .... Here, masses m1, m2, m3, ... and inductance L1, L2, L3, ... are part of heavy metal 52, and the springs (compliance) B1, B2, B3, ... and capacitors C1, C2, C3, ... are part of plastic film layer 51. In the mechanical equivalent circuit, the mass and spring have the following relationship: $m1 > m2 > m3 \ldots > mn$ and $B1 < B2 < B3 \ldots < Bn$. In the electrical equivalent circuit, the inductance and capacitor have the following relationship: $L1 > L2 > L3 \ldots > Ln$ and $C1 < C2 < C3 \ldots < Cn$. Because the characteristic impedance (acoustic impedance) of a system having equivalent circuits is determined by the ratio between mass m and compliance B or between inductance L and capacitor C, acoustic impedance $Z_0$ of the matching member 2 increases toward ultrasonic oscillator 1 or decreases toward subject 4. By combining ultrasonic oscillator 1 (which has a large acoustic impedance) with the subject (which has a smaller acoustic impedance), the acoustic impedance changes gradually. If the acoustic impedance of subject 4 is greater than that of ultrasonic oscillator 1, the acoustic impedance of the matching member is changed to increase gradually from ultrasonic oscillator 1 toward subject 4.

Individual unit layers that make up the acoustic impedance matching member can also be realized by depositing a heavy metal layer on top of the plastic layer by evaporation, sputtering or adhering the plastic and heavy metal layers after stratification. The acoustic impedance of the individual unit layers is determined by the thickness ratio between heavy metal layer 52 and plastic film layer 51.

Because it is easy to correctly determine each layer thickness, the matching member with acoustic impedance that changes according to the required mode from the side of ultrasonic oscillator 1 toward subject 4 can be configured with good reproducibility. Moreover, although ultrasonic oscillator 1 (in FIG. 1) is shown in a single plate construction, this construction can include multiple ultrasonic oscillators arranged in a one-dimensional or two-dimensional array.

We have described the preferred application mode for this invention. This invention may be applied very easily in other specific forms by persons possessing the necessary technical knowledge without departing from the spirit or essential characteristics of the following claims.

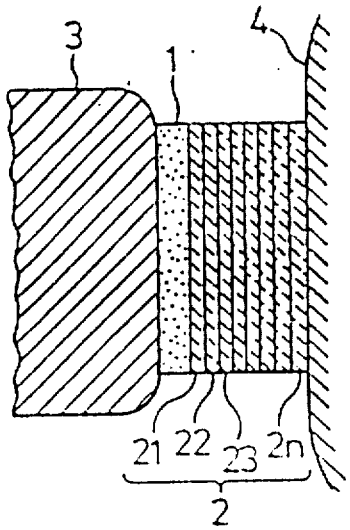

I claim:

1. An ultrasonic transducer comprising an ultrasonic oscillator device and an acoustic impedance matching member useable in contact with an ultrasonic wave radiating surface, wherein said acoustic impedance matching member consists of a plurality of layers, each layer being of a thickness less that one-quarter wavelength of an ultrasonic wave and consisting of a sublayer of plastic material and in contact therewith a sublayer of metallic material and arranged so that the sublayer of plastic material alternates with the sublayer of metallic material, wherein the ratio of thickness of the sublayer of plastic material to the thickness of the sublayer of metallic material of each successive layer of the plurality of layers gradually changes from the said radiation surface to the oscillator device.

2. The transducer of claim 1, wherein said ratio gradually increases from the radiation surface to the oscillator device.

3. The transducer of claim 1, wherein said ratio gradually decreases from the radiation surface to the oscillator device.

4. The transducer of claim 1, wherein said oscillator device includes an acoustic damper.

5. The transducer of claim 1, wherein said plastic material is selected from the group consisting of mylar, polester and polyolefine; and wherein said metallic material is selected from the group consisting of copper, chromium, nickel, iron, coblat, oxides of the foregoing metals, and nitrides of the foregoing metals.

* * * * *

UNITED STATES PATENT AND TRADEMARK OFFICE
CERTIFICATE OF CORRECTION

PATENT NO. : 4,881,212

DATED : November 14, 1989

INVENTOR(S) : Yasuhito Takeuchi

It is certified that error appears in the above-identified patent and that said Letters Patent is hereby corrected as shown below:

The title page should be deleted to appear as per attached title page.

The drawings containing figures 1-8 should be deleted to be replaces with figures 1-6 as shown on the attached sheets.

Signed and Sealed this

Nineteenth Day of June, 1990

*Attest:*

HARRY F. MANBECK, JR.

*Attesting Officer*     *Commissioner of Patents and Trademarks*

United States Patent [19]

Takeuchi

[11] Patent Number: 4,881,212
[45] Date of Patent: Nov. 14, 1989

[54] ULTRASONIC TRANSDUCER

[75] Inventor: Yasuhito Takeuchi, Tokyo, Japan

[73] Assignee: Yokogawa Medical Systems, Limited, Tokyo, Japan

[21] Appl. No.: 270,157

[22] PCT Filed: Apr. 24, 1987

[86] PCT No.: PCT/JP87/00265
§ 371 Date: Oct. 18, 1988
§ 102(e) Date: Oct. 18, 1988

[87] PCT Pub. No.: WO87/06790
PCT Pub. Date: Nov. 5, 1987

[30] Foreign Application Priority Data

Apr. 25, 1986 [JP] Japan .................. 61-96549

[51] Int. Cl.⁴ .................. H04R 1/02
[52] U.S. Cl. .................. 367/152; 310/336
[58] Field of Search .................. 310/334, 336; 73/644; 367/140, 157, 152

[56] References Cited

U.S. PATENT DOCUMENTS

| | | | |
|---|---|---|---|
| 3,979,565 | 9/1976 | McShane | 310/336 X |
| 4,366,406 | 12/1982 | Smith et al. | 310/336 X |
| 4,523,122 | 6/1985 | Tone et al. | 310/334 |
| 4,594,897 | 6/1986 | Bantz | 310/336 |
| 4,659,956 | 4/1987 | Trzaskos et al. | 310/335 |
| 4,749,900 | 6/1988 | Hadimioglu et al. | 310/334 |
| 4,795,935 | 1/1989 | Fujii et al. | 310/336 |

FOREIGN PATENT DOCUMENTS

| | | | |
|---|---|---|---|
| 2746712 | 4/1978 | Fed. Rep. of Germany | 310/334 |
| 119998 | 7/1984 | Japan | 310/336 |

Primary Examiner—Brian S. Steinberger
Attorney, Agent, or Firm—Moonray Kojima

[57] ABSTRACT

This invention is basically, an ultrasonic transducer that can be configured with good reproducibility, that includes an acoustic impedance matching member that gradually changes the acoustic impedance, and which is characterized by An acoustic impedance matching member(2) configured with multiple unit layers (21, 22, 23, . . . 2n), each layer being thinner than a quarter-wavelength of an ultrasonic wave, and each unit layer having a laminated structure make up of heavy metal(52) and plastic(51) layers with a thickness ratio set between them to change gradually from the unit layer close to the ultrasonic oscillator to the unit layer close to the subject.

5 Claims, 2 Drawing Sheets